US011607253B2

(12) United States Patent
Billard et al.

(10) Patent No.: US 11,607,253 B2
(45) Date of Patent: Mar. 21, 2023

(54) FLEXIBLE CARTILAGE REPLACEMENT

(71) Applicant: Zimmer Biomet CMF and Thoracic, LLC, Jacksonville, FL (US)

(72) Inventors: Max Holland Billard, Jacksonville, FL (US); Saddy Garcia, St. Augustine, FL (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 697 days.

(21) Appl. No.: 16/574,432

(22) Filed: Sep. 18, 2019

(65) Prior Publication Data

US 2020/0197057 A1 Jun. 25, 2020

Related U.S. Application Data

(60) Provisional application No. 62/783,587, filed on Dec. 21, 2018.

(51) Int. Cl.
*A61B 17/80* (2006.01)
*A61F 2/30* (2006.01)
*A61F 2/46* (2006.01)

(52) U.S. Cl.
CPC ...... *A61B 17/8076* (2013.01); *A61B 17/8085* (2013.01); *A61F 2/30756* (2013.01);
(Continued)

(58) Field of Classification Search
CPC . A61B 17/80; A61B 17/8066; A61B 17/8071; A61B 17/8076; A61B 17/8085; A61F 2/30756
See application file for complete search history.

(56) References Cited

U.S. PATENT DOCUMENTS 4,944,753 A * 7/1990 Burgess ................ A61B 90/00
  606/86 R
6,290,644 B1 * 9/2001 Green, II ........... A61B 17/0218
  600/209
(Continued)

FOREIGN PATENT DOCUMENTS

CN 104287817 A * 1/2015 ......... A61B 17/8038
CN 113226205 A 8/2021
(Continued)

OTHER PUBLICATIONS

"Australian Application Serial No. 2019401234, First Examination Report dated Oct. 25, 2021", 2 pgs.
(Continued)

*Primary Examiner* — Si Ming Ku
(74) *Attorney, Agent, or Firm* — Schwegman Lundberg & Woessner, P.A.

(57) ABSTRACT

To replace costal cartilage that has been surgically removed, a surgeon can implant a flexible element to connect a rib to the sternum. In some examples, the flexible element can be formed from a material having a selected durometer (e.g., a measure of material stiffness or hardness), and can be shaped to have a selected geometry (e.g., cross-sectional size and shape), to match the flexibility (e.g. resistance to bending) of the natural costal cartilage. The flexible element can connect to the rib via a rib bracket, which can be rigid, and can attach to a sternal end of the rib via one or more fasteners. The flexible element can connect to the sternum via a sternum bracket, which can also be rigid, and can also attach to the sternum via one or more fasteners. The fasteners can be screws, nails, staples, or others.

20 Claims, 16 Drawing Sheets

(52) U.S. Cl.
CPC .. *A61F 2/4618* (2013.01); *A61F 2002/30014* (2013.01); *A61F 2002/30016* (2013.01)

(56) References Cited

U.S. PATENT DOCUMENTS

| | | | |
|---|---|---|---|
| 2007/0239158 | A1 | 10/2007 | Trieu et al. |
| 2009/0248091 | A1 | 10/2009 | Teague et al. |
| 2011/0106153 | A1 | 5/2011 | Stone et al. |
| 2018/0193073 | A1 | 7/2018 | Frank et al. |
| 2020/0315675 | A1* | 10/2020 | Triana Espinel .. A61B 17/8085 |

FOREIGN PATENT DOCUMENTS

| | | | | |
|---|---|---|---|---|
| FR | 3046536 A1 * | 7/2017 | ......... | A61B 17/8023 |
| WO | WO-2020131178 A1 | 6/2020 | | |

OTHER PUBLICATIONS

"Australian Application Serial No. 2019401234, Response filed Nov. 9, 2021 to First Examination Report dated Oct. 25, 2021", 16 pgs.
"European Application Serial No. 19779692.3, Response to Communication pursuant to Rules 161(1) and 162 EPC filed Feb. 15, 2022", 27 pgs.
"International Application Serial No. PCT/US2019/051652, International Preliminary Report on Patentability dated Jul. 1, 2021", 8 pgs.
"International Application Serial No. PCT/US2019/051652, International Search Report dated Jan. 20, 2020", 5 pgs.
"International Application Serial No. PCT/US2019/051652, Written Opinion dated Jan. 20, 2020", 6 pgs.

* cited by examiner

FLEXIBLE CARTILAGE REPLACEMENT

CLAIM OF PRIORITY

This application claims the benefit of U.S. Provisional Patent Application Ser. No. 62/783,587, filed on Dec. 21, 2018, the benefit of priority of which is claimed hereby, and which is incorporated by reference herein in its entirety.

FIELD OF THE DISCLOSURE

The present disclosure relates generally to surgical replacement for costal cartilage, which connects anterior ends of a patient's ribs to the patient's sternum.

BACKGROUND OF THE DISCLOSURE

In human anatomy, costal cartilage connects the ribs to the sternum. Specifically, costal cartilage is found at anterior ends of the ribs, and medially extends from the ribs to the sternum.

In cases where the costal cartilage has been damaged, such as from accident, infection, or cancer, the surgeon can remove some or all of the costal cartilage for one or more ribs.

To preserve the integrity of the chest wall, the surgeon can reattach the affected ribs to the sternum. Typically, the surgeon uses an elongated, rigid plate to bridge an affected rib to the sternum.

Although the rigid plate stabilizes the chest wall and protects internal organs within the chest cavity, there are drawbacks to using rigid fixation between the ribs and the sternum. For example, rigid fixation can compromise a patient's ability to expand and contract the chest wall during breathing or exercising actions. In addition, the rigidity of the plate can lead to fracture, due to stresses associated with repeated bending.

Figure 1:
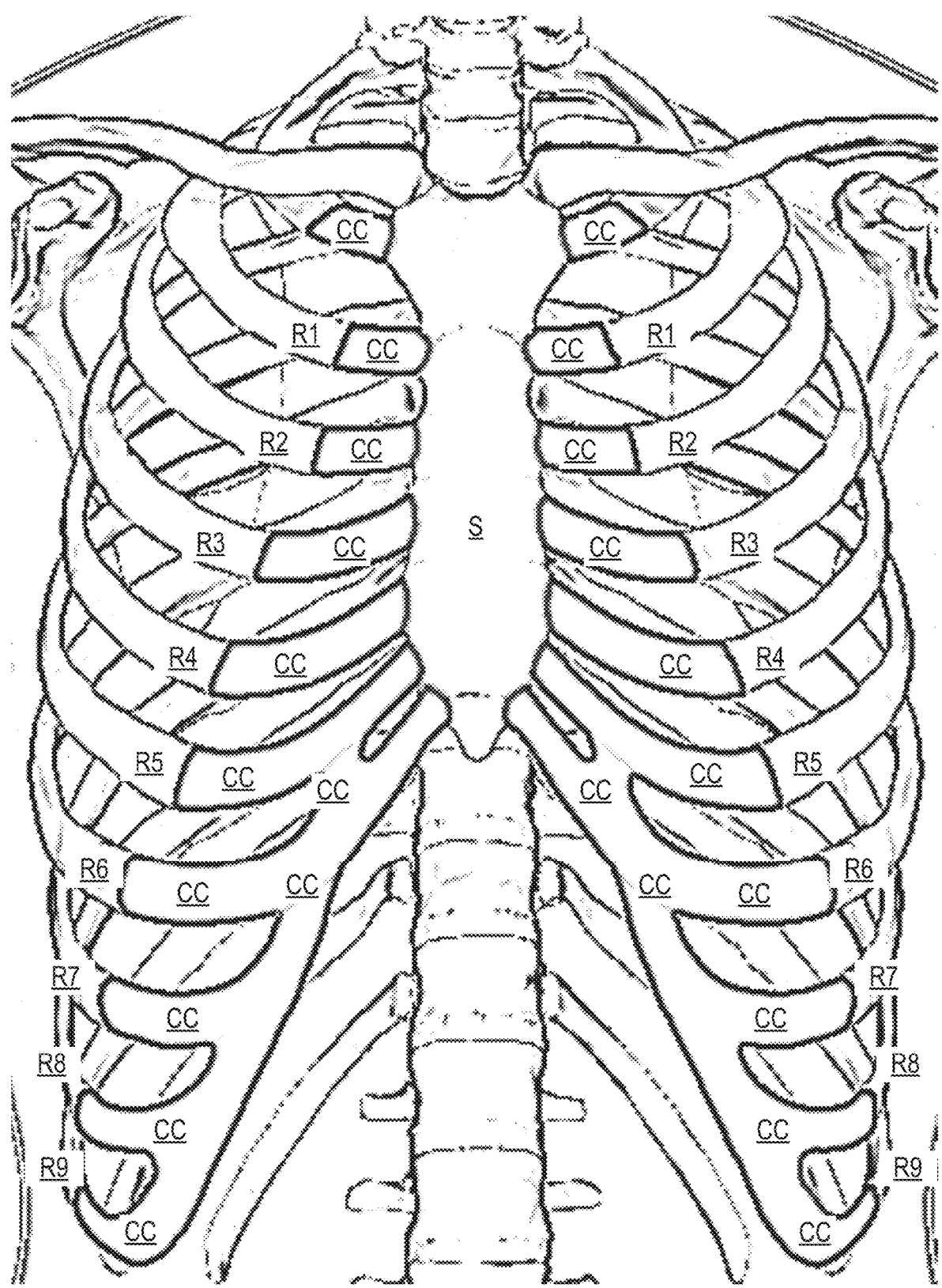
FIG. 1 shows an example of the anatomy of a typical human rib cage.

Corresponding reference characters indicate corresponding parts throughout the several views. Elements in the drawings are not necessarily drawn to scale. The configurations shown in the drawings are merely examples, and should not be construed as limiting the scope of the inventive subject matter in any manner.

DETAILED DESCRIPTION

To replace costal cartilage that has been surgically removed, a surgeon can implant a flexible element to connect a rib to the sternum. In some examples, the flexible element can be formed from a material having a selected durometer (e.g., a measure of material stiffness or hardness), and can be shaped to have a selected geometry (e.g., cross-sectional size and shape), to match the flexibility (e.g. resistance to bending) of the natural costal cartilage. The flexible element can connect to the rib via a rib bracket, which can be rigid, and can attach to a sternal end of the rib via one or more fasteners. The flexible element can connect to the sternum via a sternum bracket, which can also be rigid, and can also attach to the sternum via one or more fasteners. Examples of fasteners can include medical-grade screws, medical-grade nails, medical-grade staples, and others.

There are benefits to using the flexible element, the sternum bracket, and the rib bracket in this manner. For example, the flexibility of the flexible element can allow a patient's chest cavity to expand and contract during breathing. Such expansion and contraction is not possible for rigid fixation. As another example, because the elements are discrete and attachable, the flexible element can be supplied in different lengths, which can accommodate different anatomy sizes, and can allow a surgeon more flexibility in determining where to cut the sternal end of the rib during surgery. Other benefits are also possible.

FIG. 1 shows an example of the anatomy of a typical human rib cage. Ribs (R) surround the thoracic cavity. A sternal end of each rib (R) connects to the sternum (S) at a portion of costal cartilage (CC). The costal cartilage (CC) is flexible, which allows the chest cavity to expand and contract during breathing. The system discussed in detail below can replace all or a portion of the costal cartilage (CC) for one or more ribs (R), in accordance with some examples. In FIG. 1, each rib is numbered, such as rib 1 (R1), rib 3 (R3), and so forth. The numbering is for illustrative purposes only, and does not necessarily correspond to an absolute numbering scheme. The ribs can also be identified by the left or right side of the body, such as left rib 3. The costal cartilage can be similarly numbered, for ease of reference.

Figure 2:
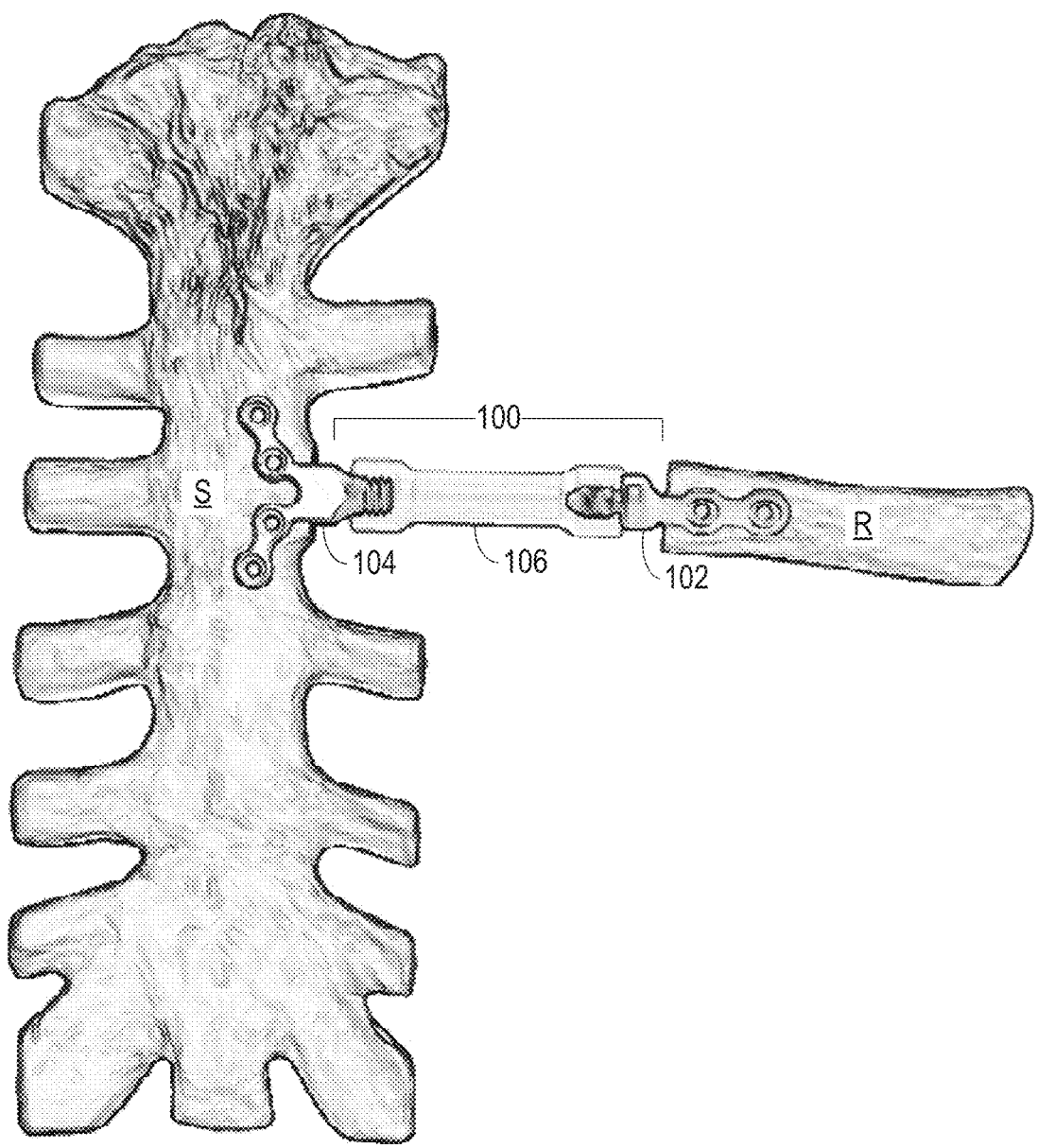
FIG. 2 shows a system for surgically attaching a rib of a patient to a sternum of the patient, in accordance with some examples.
Figure 3:
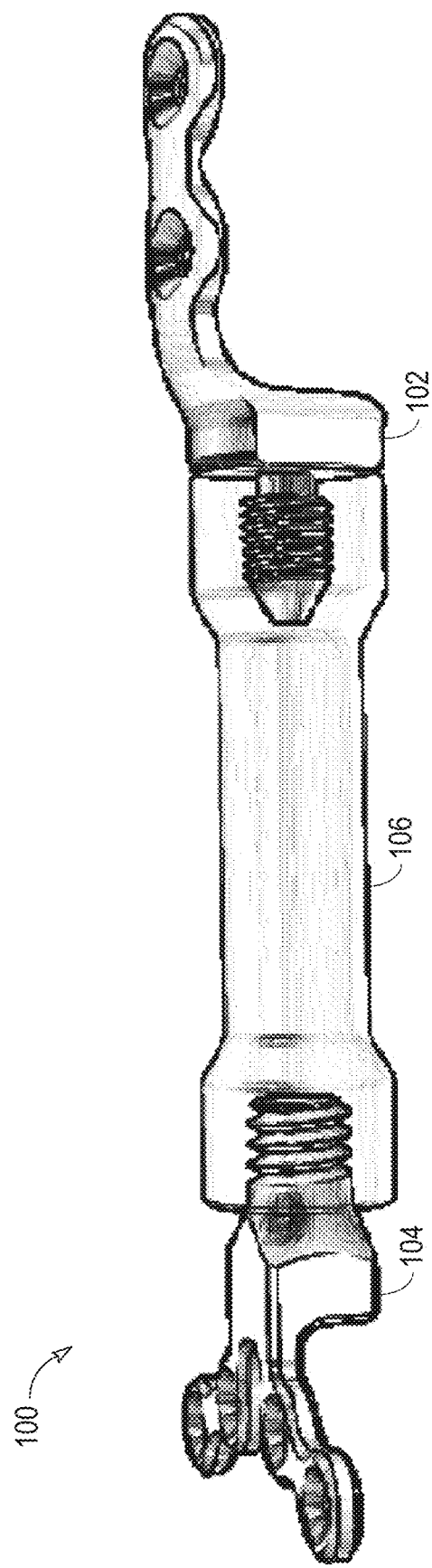
FIG. 3 shows the elements of the system removed from the anatomy of the patient, in accordance with some examples.

FIG. 2 shows a system 100 for surgically attaching a rib (R) of a patient to a sternum (S) of the patient, in accordance with some examples. FIG. 3 shows the elements of the system 100 removed from the anatomy of the patient, in accordance with some examples. The system 100 is but one example of a system that can attach a rib to a sternum; other suitable systems can also be used.

The system 100 can include a rib bracket 102 that can fixedly attach to a sternal end of the rib (R). The system 100 can further include a sternum bracket 104 that can fixedly attach to the sternum (S). The system 100 can further include a flexible element 106, formed from medical-grade silicone or another material or combination of materials, and positionable to extend between the sternum bracket 104 and the rib bracket 102. The flexible element 106 can be attachable to both the sternum bracket 104 and the rib bracket 102, or can alternatively be pre-attached to one (or both) of the sternum bracket 104 or the rib bracket 102. Each of these three elements is described in detail below.

Figure 4:
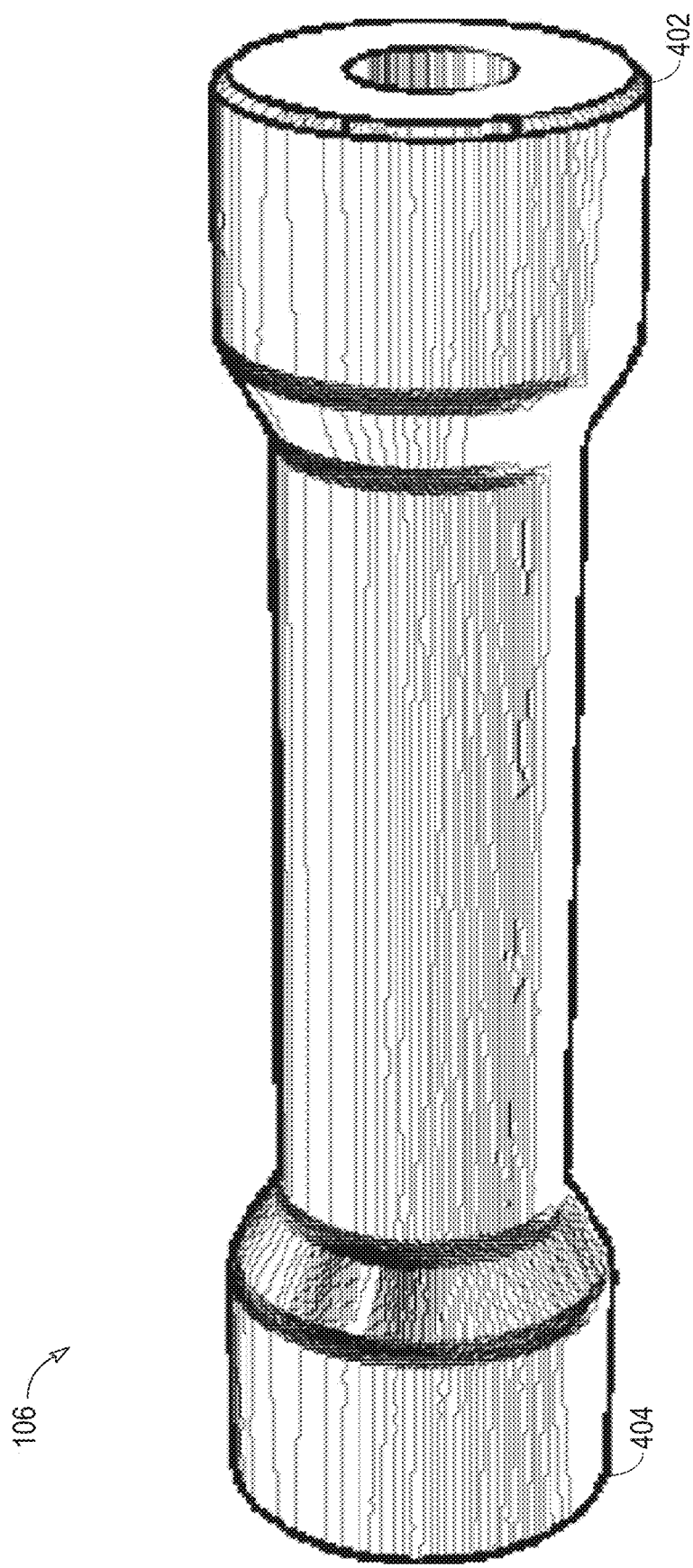
FIG. 4 shows a flexible element of the system of FIGS. 2-3, in accordance with some examples.

FIG. 4 shows a flexible element 106 of the system of FIGS. 2-3, in accordance with some examples. The configuration of FIG. 4 is but one example of a flexible element 106; other suitable configurations can also be used.

The structure and function of the flexible element 106 can be defined by various physical properties or characteristics, including, but not limited to, durometer, geometry, and flexibility. Durometer is a measure of material stiffness or hardness. Harder materials have a higher durometer than softer materials. Geometry includes cross-sectional size and shape. Flexibility is a resistance to bending. Although flexibility can be dependent on direction, it should be understood that for the examples discussed in this document, the flexibility is taken to be in a direction that allows for expansion and contraction of a chest cavity.

Flexibility is related to both durometer and geometry, but in a manner that can be difficult to express in a closed-form mathematical expression. In general, increasing an element's durometer can decrease the flexibility of the element. In general, increasing an element's thickness can also decrease the flexibility of the element in a particular direction. In addition, the geometry of an element involves more than just the element's thickness. For example, a cylindrical tube or an I-beam can be considerably stiffer than what would be expected based on the wall thickness of the tube or beam. Although flexibility is difficult to represent in a closed-form expression, the flexibility can be relatively straightforward to measure or simulate. One of ordinary skill in the art can readily simulate or measure the flexibility of a particular element, given the element's material and shape.

In some examples, the flexible element 106 can have a durometer and a geometry that are selected such that the flexible element 106 has a flexibility that substantially matches a flexibility of natural human costal cartilage. As used in this document, the term substantially is intended to mean that the flexibilities match to within a specified tolerance, such as 1%, 5%, 10%, or another suitable value. In some cases, the flexible elements 106 may only be available in a finite number of off-the-shelf configurations, with durometer and sizes/shapes that are constrained to a finite number of discrete values. For these cases, the combination of elements with these discrete values may get as close as possible to the desired value of flexibility. For example, the flexibility of the flexible element 106 can be selected to match an expected flexibility of a particular patient, while accounting for age of the patient, sex of the patient, health issues of the patient, and so forth, and additionally accounting for a discrete number of off-the-shelf combinations of durometer and geometry.

By substantially matching the flexibility of the flexible element 106 to that of natural human costal cartilage, the flexible element 106 can mimic the performance of the natural human costal cartilage. For example, when a patient inhales, the patient's muscles exert a particular force to produce a particular deformation of the chest wall. It is expected that when a flexible element 106 having similar flexibility as natural human costal cartilage is implanted, the patient can inhale by exerting similar forces as before the patient's costal cartilage was replaced. Consequently, after surgery, the patient can breathe in roughly the same manner before surgery.

In some examples, the flexible element 106 can have a cross-sectional shape that includes one of round, oval, rectangular, or oblong. In the drawings of FIGS. 2-4, the cross-sectional shape is circular, but other cross-sectional shape can also be used, including irregular shapes.

In some examples, the flexible element 106 can be tubular, with a hollow interior extending from a first end 404 of the flexible element 106 to a second end 402 of the flexible element 106. In other examples, the flexible element 106 can have a solid interior between the first end 404 of the flexible element 106 and the second end 402 of the flexible element 106. In still other examples, the flexible element 106 can have an interior that is partially hollow and partially solid. For example, a first longitudinal portion of the flexible element 106 can have a hollow interior, while a second longitudinal portion of the flexible element can have a solid interior. In still other examples, the flexible element 106 can be formed to include porous and/or mesh materials. For example, the flexible element 106 can be formed using three-dimensional printing techniques, which can produce material having a sponge-like quality. The porous and/or mesh material can be used as all or part of the tubular configuration, and/or all or part of the solid-interior configuration, and/or a full solid interior configuration formed from the porous and/or mesh material. Each configuration can also have cross-sectional shapes that include one of round, oval, rectangular, oblong, or irregular.

In some examples, the flexible element 106 can have a durometer that substantially matches a durometer of natural human costal cartilage and a geometry that substantially matches a geometry of natural human costal cartilage. For these examples, because flexibility includes a combination of durometer and geometry, the flexibility of the flexible element 106 can also substantially match a flexibility of natural human costal cartilage. For these examples, the flexible element 106 can closely resemble the shape and consistency of the costal cartilage that is being replaced. In some of these examples, the flexible element 106 can be formed from medical-grade silicone with a durometer that matches, or substantially matches, a durometer of natural human costal cartilage.

In some examples, it may be convenient to have off-the-shelf flexible elements 106 that are shaped to match an "average" rib shape, for a particular rib of a set of ribs. For these examples, for a specified rib of the plurality of ribs in the human anatomy, the geometry of the natural human costal cartilage can be based on an average patient size determined from measurements corresponding to a plurality of patients. As a specific example, CT scans or MRI scans of the anatomies of a population (e.g., a sample of 500 patients) can be analyzed to determine a so-called "standard" rib size and shape for rib 1, a "standard" size and shape for rib 2, and so forth, for each rib in the human anatomy. In some examples, the "standard" sizes can also be applied to age and/or gender. For example, flexible elements 106 could be provided in a standard "child" size and shape and a standard "adult" size and shape, for males and females, for each rib.

In some examples, it may be convenient to form the flexible element 106 to match the size and shape of an individual patient. This can be referred to as patient matching. For these examples, the geometry of the patient can be determined from a CT scan or an MRI scan of the patient. The flexible element 106 can then be formed in a suitable manner, such as by three-dimensional printing or molding. In some of these examples, the flexible element 106 can be formed from a material or combination of materials that, collectively, have substantially the same durometer as natural human costal cartilage. Similarly, the rib bracket 102 and the sternum bracket 104 can also be formed in a patient-specific manner, such as by three-dimensional printing or molding a shape determined from a CT scan or an MRI scan of the patient.

The flexible element 106 can be attached to the brackets in one of four configurations. In a first configuration, the flexible element 106 can have a first end 404 that is connectable to the sternum bracket 104 and a second end 402 that is connectable to the rib bracket 102. In a second configuration, the flexible element 106 can have a first end 404 that is pre-attached to the sternum bracket 104 and a second end 402 that is connectable to the rib bracket 102. In a third configuration, the flexible element 106 can have a first end 404 that is connectable to the sternum bracket 104 and a second end that is pre-attached to the rib bracket 102. These first three configurations allow a surgeon to reposition the brackets and flexible element 106 as needed during surgery. A fourth configuration, if the surgeon does not need to significantly reposition the brackets and flexible element 106 during surgery, is that the flexible element 106 can have a first end 404 that is pre-attached to the sternum bracket 104 and a second end 402 that is pre-attached to the rib bracket 102. This fourth configuration can be used for patient-matched options.

In conforming with the first configuration above, the flexible element 106, the rib bracket 102, and the sternum bracket 104 can be supplied decoupled to facilitate the selection of the length or durometer of the flexible element 106 from a kit or system during surgery.

In conforming with the first and third configurations above, the flexible element 106 can have a first end 404 that is connectable to the sternum bracket 104 via one of mating fastener threads, a press fit that includes at least one retaining barb, a T-slot, clamping, crimping, one or more hooks, a cross pin, or any suitable connection technique.

In conforming with the first and second configurations above, the flexible element 106 can have a second end 402 that is connectable to the rib bracket 102 via one of mating fastener threads, a press fit that includes at least one retaining barb, a T-slot, clamping, crimping, one or more hooks, a cross pin, or any suitable connection technique.

In conforming with the second and fourth configurations above, the flexible element 106 can have a first end 404 that is overmolded onto to at least a portion of the sternum bracket 104. Other connection techniques can also be used, including any or all of the above.

In conforming with the third and fourth configurations above, the flexible element 106 can have a second end 402 that is overmolded onto to at least a portion of the rib bracket 102. Other connection techniques can also be used, including any or all of the above.

In examples for which the flexible element 106 is intended to connect with external threads on a bracket, the flexible element 106 can optionally be provided without corresponding internal threads, and can be self-threading. For these examples, the flexible element 106 can be formed from a material that is soft enough to conform over the external threads of the bracket. When the flexible element 106 is forced against the bracket, the material of the flexible element 106 can deform around the external threads of the bracket, and dynamically form the corresponding internal threads of the flexible element 106. In some examples, the threads of the flexible element 106 can be dynamically formed without twisting the flexible element 106 with respect to the bracket. In other examples, the threads of the flexible element 106 can be dynamically formed by pushing and twisting the flexible element 106 with respect to the bracket. For these examples, the threads of the bracket can function like a barb or several barbs, and can prevent the flexible element 106 from being withdrawn from the threads of the bracket.

Figure 5:
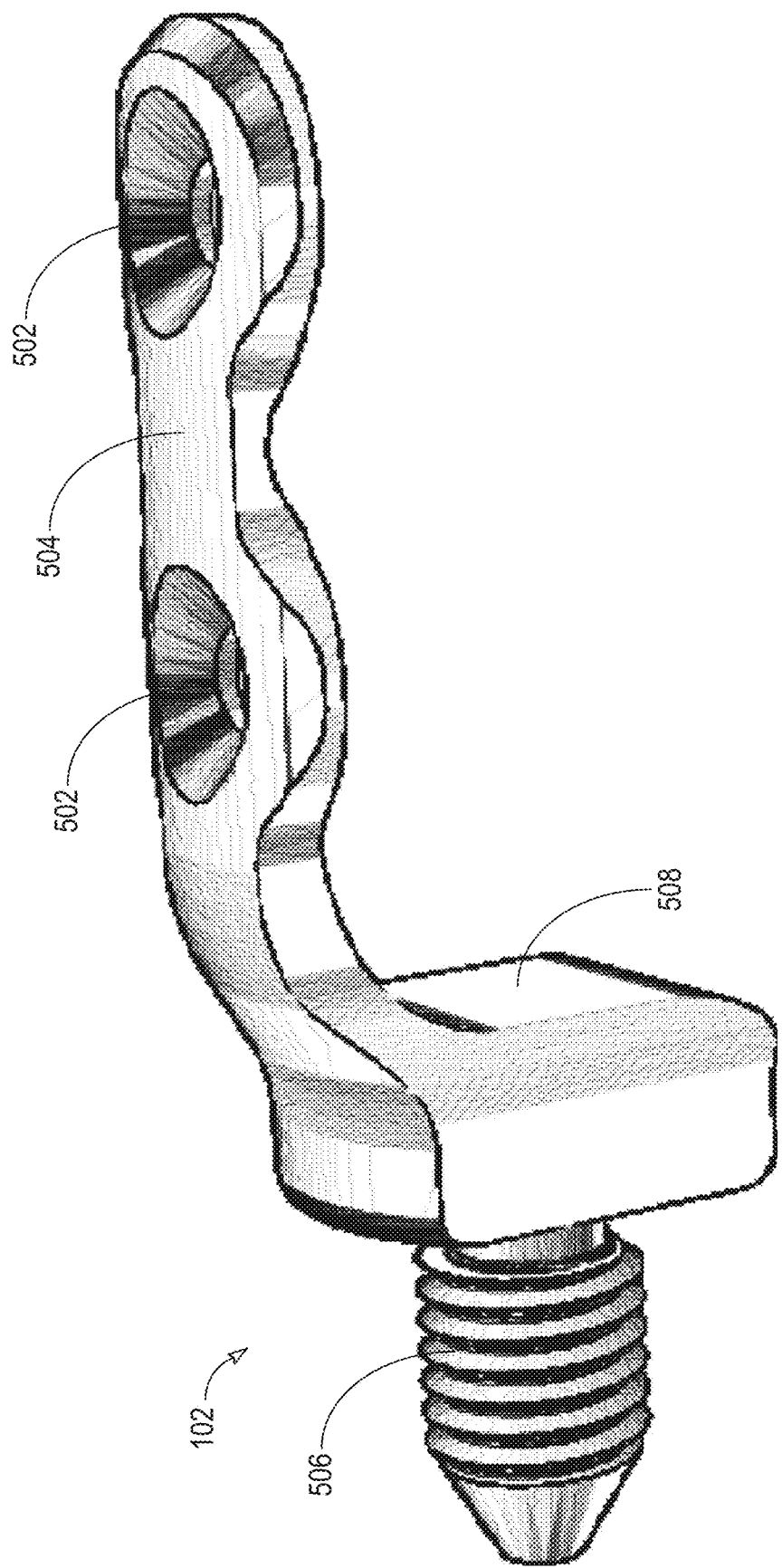
FIG. 5 shows a rib bracket of the system of FIGS. 2-3, in accordance with some examples.

FIG. 5 shows a rib bracket 102 of the system of FIGS. 2-3, in accordance with some examples. The rib bracket 102 can fixedly attach to a resected sternal end of a rib. The rib bracket 102 can be attachable to the flexible element 106, or can be provided as pre-attached to the flexible element 106. The configuration of FIG. 5 is but one example of a rib bracket 102; other suitable configurations can also be used (including an additional configuration shown in FIGS. 6-7 and described below.)

In some examples, the rib bracket 102 can include at least one rib fastener hole 502 shaped and sized to accommodate a rib fixation fastener (not shown). In some of these examples, the rib bracket 102 can include a plurality of rib fastener holes 502, each rib fastener hole 502 being shaped and sized to accommodate a rib fixation fastener (not shown). In some of these examples, the rib fastener holes 502 can be arranged in a line that extends parallel to the rib. Other positions for the rib fastener holes 502 can also be used, including along a line that is skewed with respect to the rib, or a non-linear arrangement, such as along a curve, or in an irregular pattern. In some examples, the rib fastener holes 502 can be countersunk into a body 504 of the rib bracket 102. The countersinking can help center the rib fixation fasteners upon insertion, and can help prevent complications from sharp or jagged edges from the screw heads. In some examples, polyaxial screws can be used, which can be insertable at one of several angles, including off-axis angles. The rib bracket 102 can attach to the rib so that the rib fastener holes 502 face inward toward an interior of the chest cavity, face outward away from the chest cavity, or face along any suitable direction around a circumference (e.g., a cross-sectional perimeter) of the resected sternal end of the rib. In other examples, the rib bracket 102 can lack rib fastener holes 502, and can be secured to a rib by a press fit, such as by clamping a portion of bone between two elements. In still other examples, a stem can be pressed into the cancellous bone of the rib, in a manner similar to insertion of a typical hip stem.

For configurations in which the rib bracket 102 is attachable to the flexible element 106, the rib bracket 102 can include a male threaded portion 506 that can threadedly attach to a corresponding female threaded portion at a second end of the flexible element 106. In some examples, the male threaded portion 506 can face away from the rib toward the sternum when the flexible element 106 is attached to the rib bracket 102. In some examples, the male threaded portion 506 can be colinear with a central axis of the rib, when the rib bracket 102 is attached to the rib. As an alternative to the male threaded portion 506, the rib bracket 102 may instead include a female threaded portion that can attach to a corresponding male threaded portion at the second end of the flexible element 106. As an alternative to threads, the rib bracket 102 may form a press (friction) fit with a corresponding portion of the flexible element 106, and may optionally include one or more retaining barb.

In some examples, the rib bracket 102 can include a ledge 508 shaped to fit against the resected sternal end of the rib. In some examples, the ledge 508 can be flat. In some examples, the ledge 508 can be parallel to the resected sternal end of the rib. In some examples, the ledge 508 can be orthogonal to a central axis of the rib.

The rib bracket 102 shown in FIGS. 2, 3, and 5 can attach to an exterior of the rib. Specifically, a surgeon can insert a rib fixation fastener, through a corresponding rib fastener hole 402, through an exterior surface of the rib. As an alternative, the rib bracket can include an element that can insert into a resected sternal end of the rib, at least partially into an interior of the rib. Such an element can help stabilize and strengthen the rib bracket.

Figure 6:
FIG. 6 shows an alternative rib bracket, in accordance with some examples.

FIG. 6 shows an alternative rib bracket 102A, in accordance with some examples. In this example, the rib bracket 102A can fixedly attach to a resected sternal end of a rib (R), and can include an optional additional element that can insert into an interior of the rib (R). In the same manner as for the rib bracket 102, the rib bracket 102A can be attachable to the flexible element 106, or can be provided as pre-attached to the flexible element 106.

Figure 7:
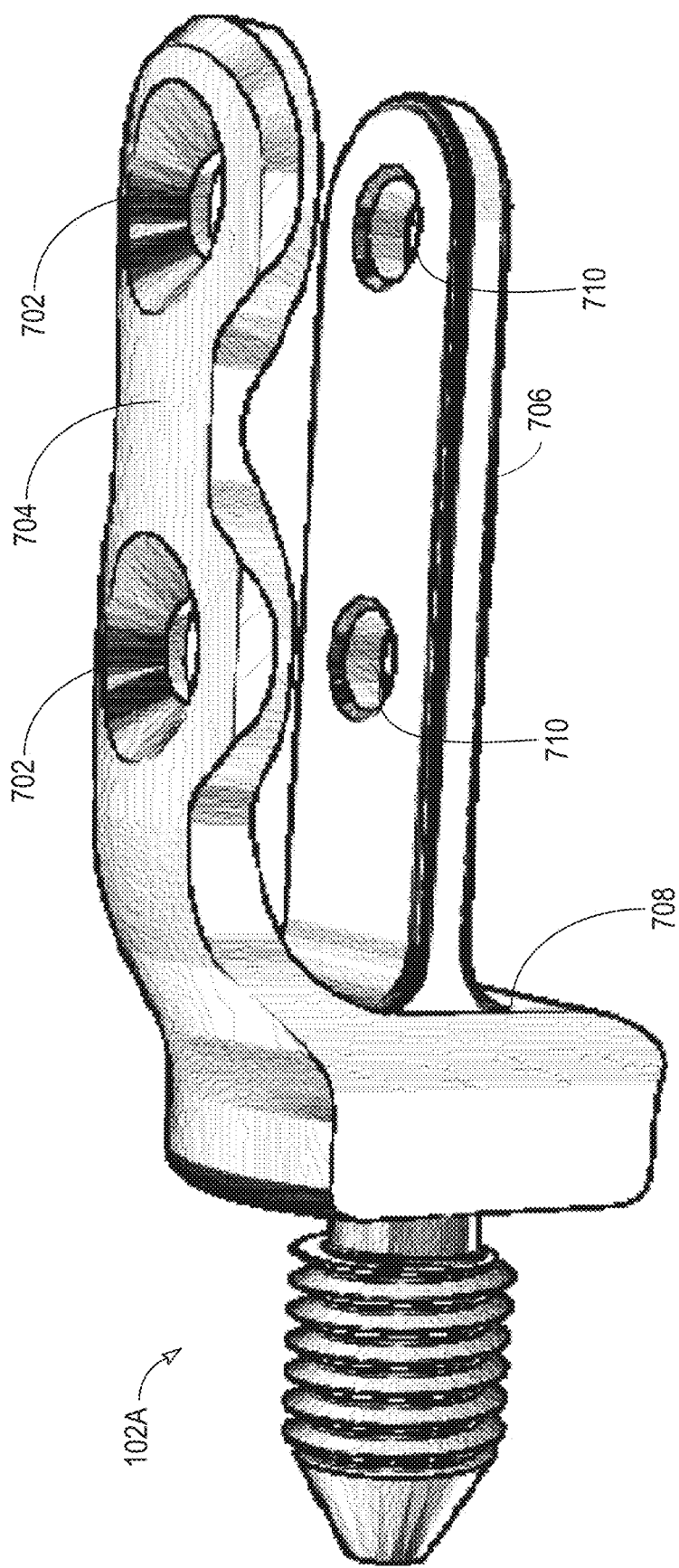
FIG. 7 shows the detail of the rib bracket of FIG. 6, in accordance with some examples.

FIG. 7 shows the detail of the rib bracket 102A of FIG. 6, in accordance with some examples. Compared with the rib bracket 102 of FIGS. 2, 3, and 5, the rib bracket 102A additionally includes an optional intramedullary portion 706 that can extend from the ledge 708. The intramedullary portion 706 can extend at least partially into an exposed interior portion of the rib, so that at least some of the intramedullary portion 706 is positioned within the rib when the rib bracket 102.A is attached to the rib. In some examples, the intramedullary portion 706 can be parallel to a body 704 of the rib bracket 102A. In some examples, the intramedullary portion 706 can include one or more fastener holes 710. In some examples, one of more of the fastener holes 710 can optionally be colinear with corresponding rib fastener holes 402.

Figure 8:
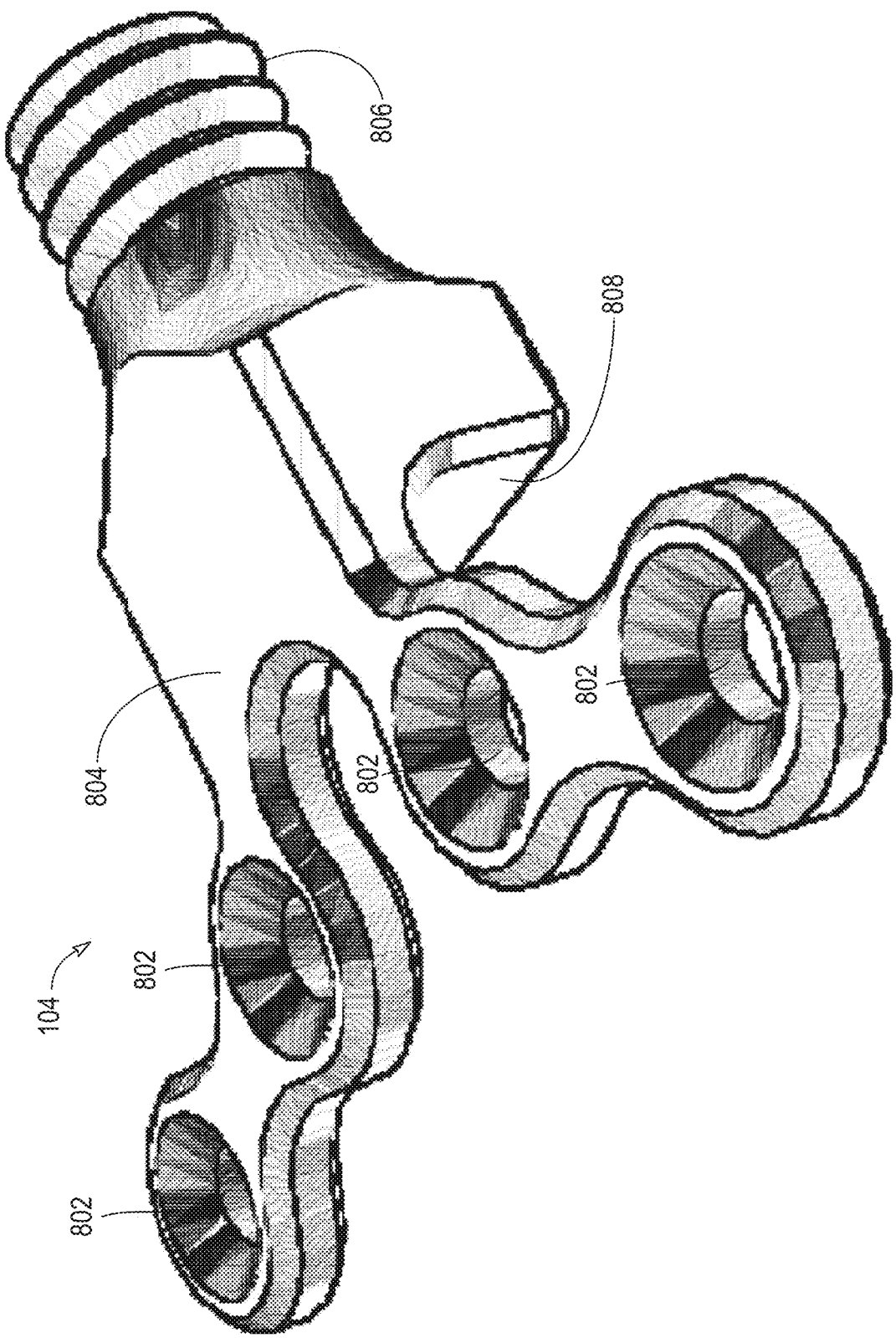
FIG. 8 shows a sternum bracket of the system of FIGS. 2-3, in accordance with some examples.

FIG. 8 shows a sternum bracket 104 of the system of FIGS. 2-3, in accordance with some examples. The sternum bracket 104 can be attachable to the flexible element 106, or can be provided as pre-attached to the flexible element 106. The configuration of FIG. 8 is but one example of a sternum bracket 104; other suitable configurations can also be used (including additional configurations shown in FIGS. 8 and 9, as described below.)

In some examples, the sternum bracket 104 can include at least one sternum fastener hole 802 shaped and sized to accommodate a sternum fixation fastener (not shown). In some of these examples, the sternum bracket can include a plurality of sternum fastener holes 802, each sternum fastener hole 802 being shaped and sized to accommodate a sternum fixation fastener. In some examples, such as in FIG. 8, the sternum fastener holes 802 can be arranged along a curve that has a tangent at its center that is orthogonal to a plane of the rib. In other examples, such as the examples shown in FIGS. 9-12 and discussed below, the sternum fastener holes 802 can be arranged in a line that extends in a plane of the rib. As a further alternative, the sternum fastener holes 802 can be arranged in a non-linear fashion. In some examples, the sternum fastener holes 802 can be countersunk into a body 804 of the sternum bracket 104. The countersinking can help center the sternum fixation fasteners upon insertion, and can help prevent complications from sharp or jagged edges from the fastener heads. The sternum bracket 104 can attach to the sternum so that the sternum fastener holes 802 face anteriorly or posteriorly. In other examples, the sternum bracket 104 can lack sternum fastener holes 802, and can be secured to the sternum by a press fit, such as by clamping a portion of the sternum between two elements. In still other examples, a stem can be pressed into the cancellous bone of the rib, in a manner similar to insertion of a typical hip stem.

For configurations in which the sternum bracket 104 is attachable to the flexible element 106, the sternum bracket 104 can include a male threaded portion 806 that can threadedly attach to a corresponding female threaded portion at a first end of the flexible element 106. In some examples, the male threaded portion 806 can face away from the sternum toward the rib when the flexible element 106 is attached to the sternum bracket 104. As an alternative to the male threaded portion 806, the sternum bracket 104 may instead include a female threaded portion that can attach to a corresponding male threaded portion at the first end of the flexible element 106. As an alternative to threads, the sternum bracket 104 may form a press (friction) fit with a corresponding portion of the flexible element 106, and may optionally include one or more retaining barb.

In some examples, the sternum bracket 104 can include a ledge 808 shaped to fit against an intercostal region of the sternum. In some examples, the ledge 808 can be flat.

Figure 9:
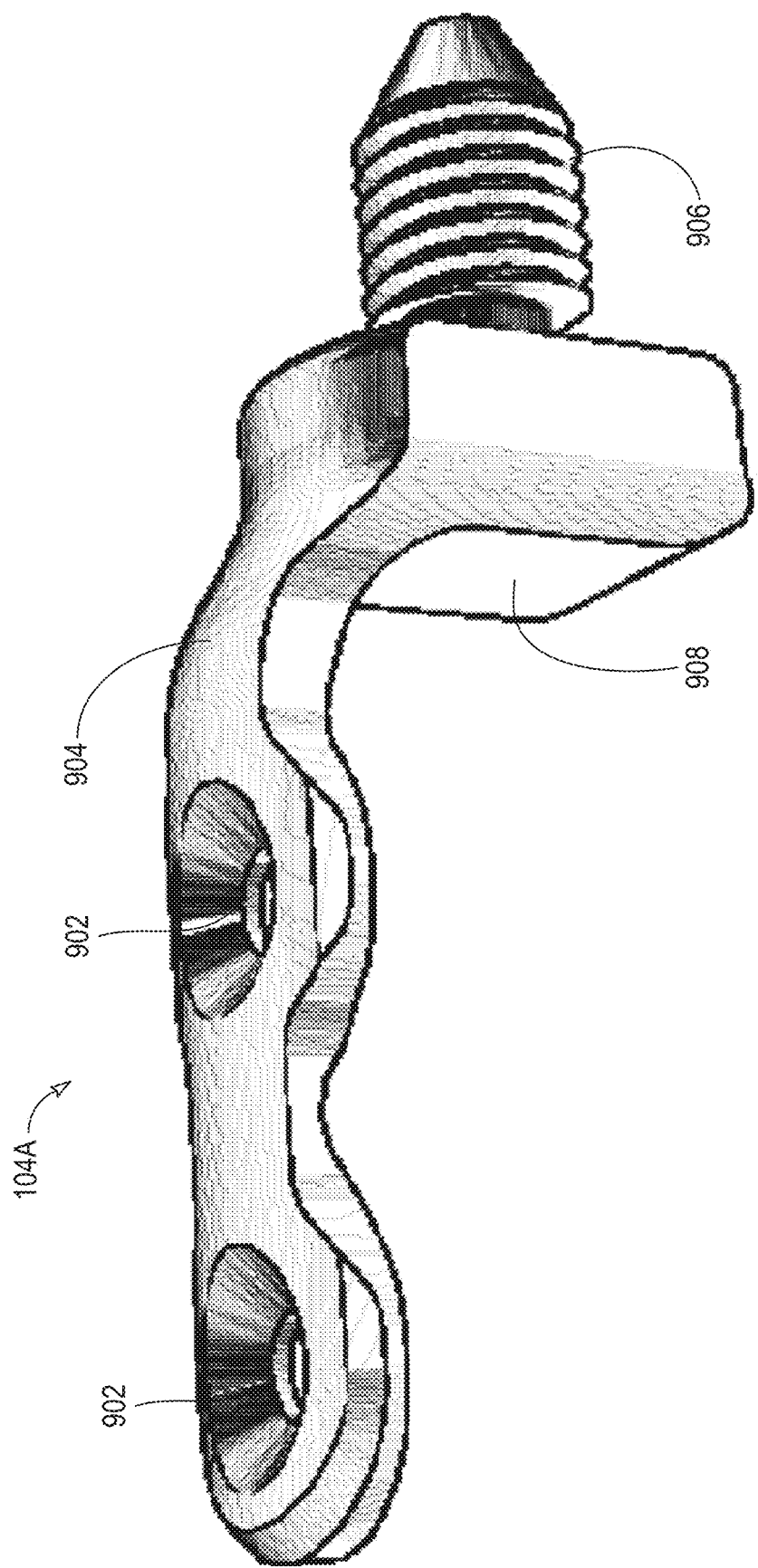
FIG. 9 shows an alternative sternum bracket, in accordance with some examples.

FIG. 9 shows an alternative sternum bracket 104A, in accordance with some examples. The sternum bracket 104A can be attachable to the flexible element 106, or can be provided as pre-attached to the flexible element 106. The sternum bracket 104A is compatible with all the configurations of rib brackets discussed above. The configuration of FIG. 9 is but one example of a sternum bracket 104A; other suitable configurations can also be used (including an additional configuration shown in FIG. 9, as described below.)

In contrast with the configuration of FIG. 8, in which the sternum fastener holes 802 are arranged along a curve that has a tangent at its center that is orthogonal to a plane of the rib, the sternum fastener holes 902 in the configuration of FIG. 9 can be arranged in a line that extends in a plane of the rib.

Whereas the surface area of a rib is relatively limited, so that the rib fastener holes are typically confined to reside along a line, the surface area of the sternum is relatively large, so that there are many more options for positioning the sternum fastener holes. It will be understood that other suitable arrangements for the sternum fastener holes 902 of the sternum bracket 104A can also be used.

In some examples, the sternum fastener holes 902 can be countersunk into a body 904 of the sternum bracket 104A. The male threaded portion 906 and the ledge 908 function in a similar manner to the male threaded portion 806 and the ledge 808 shown in FIG. 8, including all the alternative options discussed above.

In the configurations of FIGS. 2-9, the system 100 can surgically attach a single rib of a patient to the sternum of the patient. As an alternative, there are configurations in which the system can attach multiple ribs to the sternum.

Figure 10:
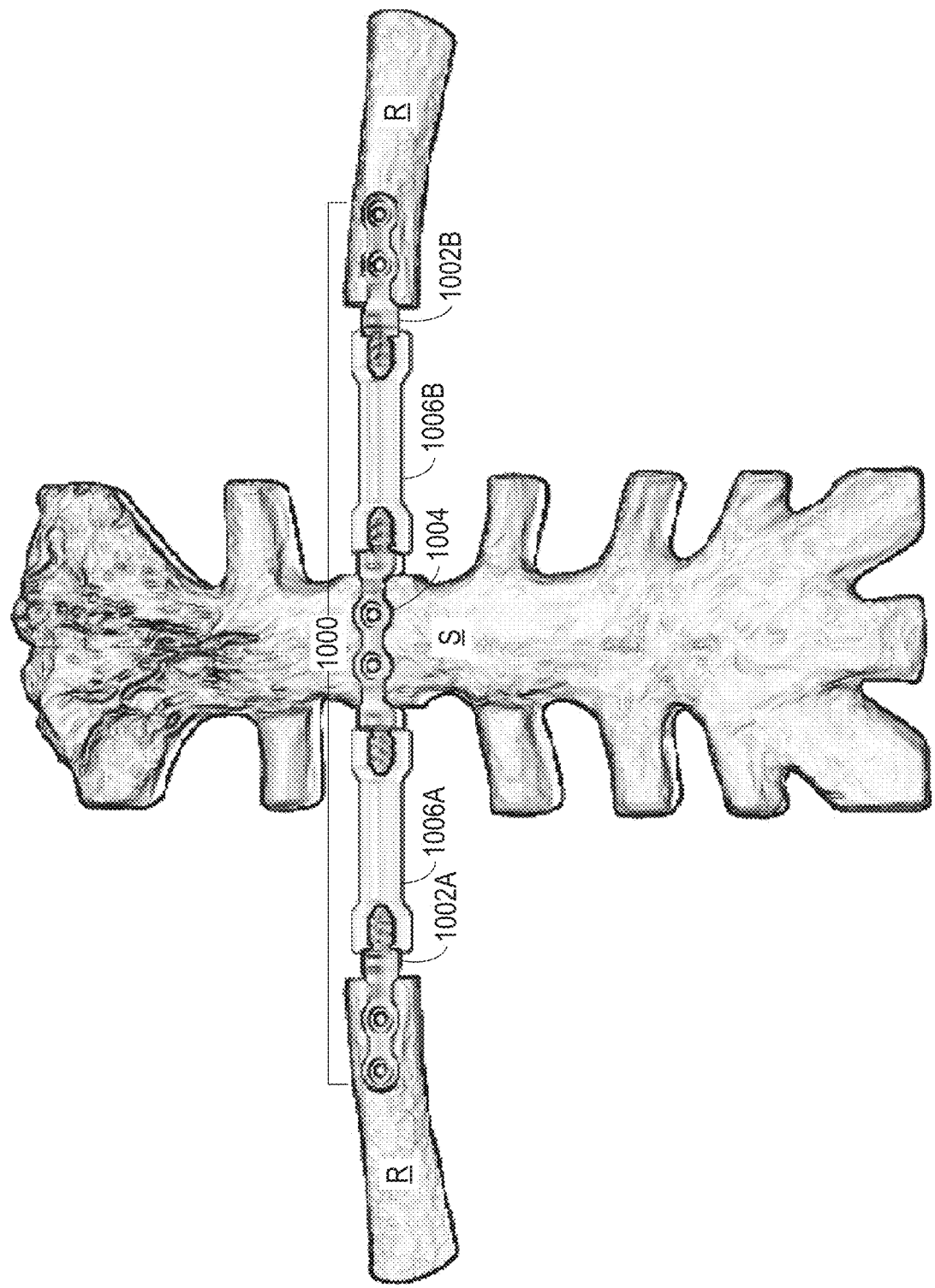
FIG. 10 shows a system for surgically attaching multiple ribs of a patient to a sternum of the patient, in accordance with some examples.

FIG. 10 shows a system 1000 for surgically attaching multiple ribs (R) of a patient to a sternum (S) of the patient, in accordance with some examples. The system 1000 is but one example of a system that can attach multiple ribs to the sternum; other suitable systems can also be used.

The system 1000 can include a sternum bracket 1004 that is sized to extend across a lateral dimension (e.g. left-to-right) of the sternum at a first longitudinal location along the sternum. The sternum bracket 1004 can attach the sternum to two flexible elements, on opposite sides of the sternum. The sternum bracket 1004 can include fasteners holes positioned in a manner similar to the configurations discussed above with respect to sternum brackets that attach to a single flexible element.

The system 1000 can include first rib bracket 1002A that can fixedly attach to a resected sternal end of a first rib of a plurality of ribs of the patient. A first flexible element 1006A can be positionable to extend between the sternum bracket 1004 and the first rib bracket 1002A.

The system 1000 can further include a second rib bracket 1002B that can fixedly attach to a resected sternal end of a second rib of the plurality of ribs of the patient. The first and second ribs can be positioned at the first longitudinal location (e.g., the same numbered rib, such as rib 1, rib 2, and so forth) along the sternum on opposite sides of the sternum (e.g., at the same rib number on the left and right sides of the sternum). A second flexible element 1006B can be positionable to extend between the sternum bracket 1004 and the second rib bracket 1002B.

All the flexible elements discussed above can attach a single sternum bracket to a single rib bracket. As an alternative, a flexible element can instead attach a single sternum bracket to multiple rib brackets. For example, in human anatomy, the lower ribs are naturally bridged together, so that the costal cartilage corresponding to several ribs attached to the sternum at a single longitudinal location at the sternum. For cases in which the costal cartilage of some of these lower ribs is replaced, the flexible element can mimic the connection pattern of the natural costal cartilage. For example, a single flexible element can attach to a single sternum bracket, and can include one or more bridging members to allow the flexible element to attach to multiple rib brackets. Such bridging members can also be used to allow a single flexible element to attach to multiple sternum brackets and to attach to multiple rib brackets. Other configurations for the bridging members can also be used.

All the configurations discussed above pertain to cases in which the costal cartilage is replaced, but the sternum is left intact. As an alternative, there can be instances in which some or all of the sternum is replaced. To address these cases, the sternum replacement can include threads that are formed integrally with the sternum replacement. In this manner, the flexible element can attach directly to the sternum replacement, rather than utilize a sternum bracket to form the attachment. The sternum replacement can alternatively include a press-fit surface, or any of the other attachment mechanisms discussed above with respect to the interface between a sternum bracket and a flexible element.

Figure 11:
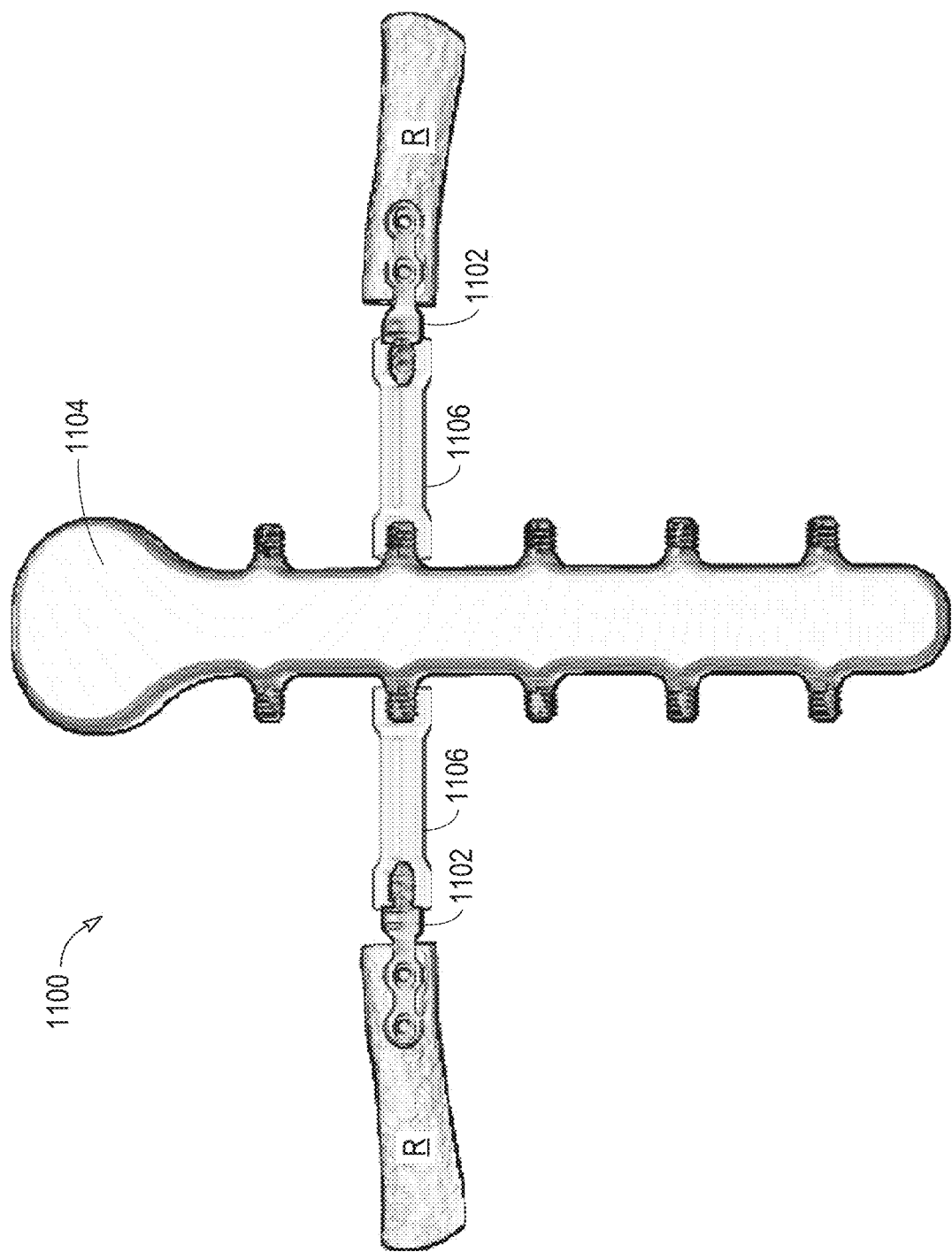
FIG. 11 shows a system for surgically attaching one or more ribs of a patient to a sternum replacement implant, in accordance with some examples.

FIG. 11 shows a system 1100 for surgically attaching one or more ribs (R) of a patient to a sternum replacement implant 1104, in accordance with some examples. In FIG. 11, the sternum replacement 1104 is a full artificial sternum, but a partial sternum replacement implant can also be used. The system 1100 is but one example of a system for surgically attaching one or more ribs of a patient to a sternum replacement implant of the patient; other suitable systems can also be used.

The system 1100 can surgically attach a rib of a patient to a sternum of the patient. A sternum replacement implant 1104 can replace at least a portion of the sternum. A rib bracket 1102 can fixedly attach to a sternal end of the rib. A flexible element 1106 can be positionable to extend between the sternum replacement implant 1104 and the rib bracket 1102. Each flexible element 1106 can be attachable to both the sternum replacement implant 1104 and a rib bracket 1102, or can alternately be pre-attached to one of the sternum replacement implant 1104 or the rib bracket 1102, as discussed above.

Figure 12:
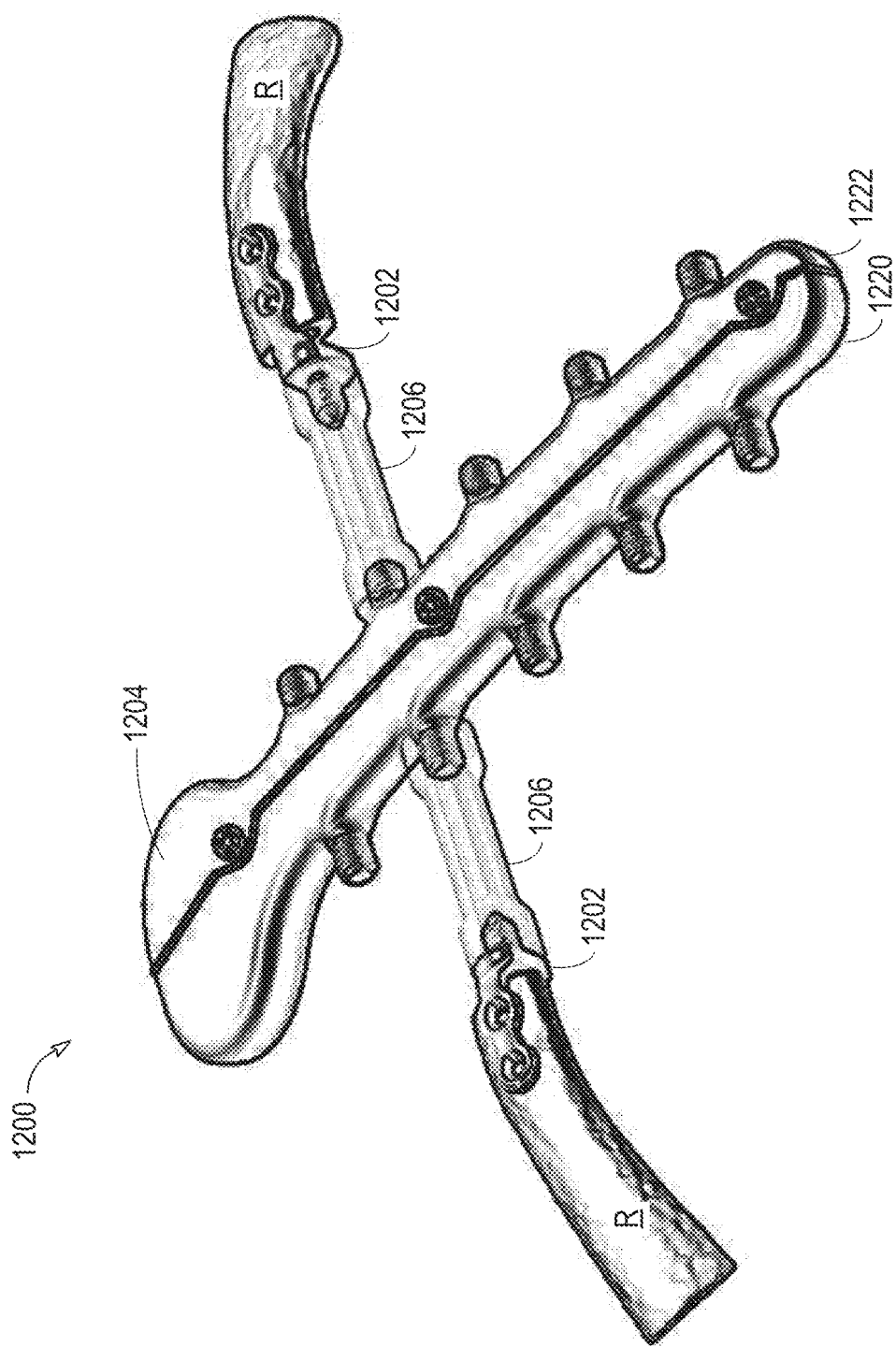
FIG. 12 shows a system for surgically attaching one or more ribs of a patient to a sternum replacement implant, in accordance with some examples.

FIG. 12 shows a system 1200 for surgically attaching one or more ribs (R) of a patient to a sternum replacement implant 1204, in accordance with some examples.

Several elements of the system 1200 are similar in structure and function to corresponding elements in the system 1100 of FIG. 11. A sternum replacement implant 1204 can replace at least a portion of the sternum. A rib bracket 1202 can fixedly attach to a sternal end of the rib. A flexible element 1206 can be positionable to extend between the sternum replacement implant 1204 and the rib bracket 1202. Each flexible element 1206 can be attachable to both the sternum replacement implant 1204 and a rib bracket 1202, or can alternately be pre-attached to one of the sternum replacement implant 1204 or the rib bracket 1202, as discussed above.

Compared with the system 1100 of FIG. 11, the sternum replacement implant 1204 can additionally include a first half 1220 and a second half 1222, the first and second halves being laterally separable and reattachable. Such reattachability can allow a surgeon to access the organs within the rib cage without cutting through the sternum or sternum replacement implant, which can help reduce the trauma associated with such a surgery.

In some examples, the flexible element and/or the brackets can be pre-shaped to mimic the shape or contour of a particular rib, particular cartilage, or a combination of a particular rib and particular cartilage. In some examples, the flexible element and/or the brackets can be made available in shapes that are tailored for use with one particular rib (first rib R1, third rib R3, and so forth) and one particular side of the body (left or right). The various sizes and shapes can optionally be included in a kit or system, which can span the full range of a patient's ribs. In some examples, the flexible element and/or the brackets can be shaped, during surgery but prior to implantation, to mimic the shape or contour of a particular rib.

In some examples, all or one or more portions of the flexible element and/or one or more portions of a bracket can be bent, such as by a rod bender or other shaping tool, to mimic the natural contour of a particular rib. For example, if a particular rib extends from the sternum at a twenty degree angle, the surgeon can use a rod bender or other shaping tool to bend a portion of the sternum bracket, so that the bent portion extends from the sternum at twenty degrees. In some examples, the bent portion can include the male threaded portion. Similarly, the surgeon can use a rod bender or other shaping tool to shape a male threaded portion of a rib bracket. In some examples, the surgeon can use a rod bender or other shaping tool to shape all or a portion of the flexible element.

Figure 13:
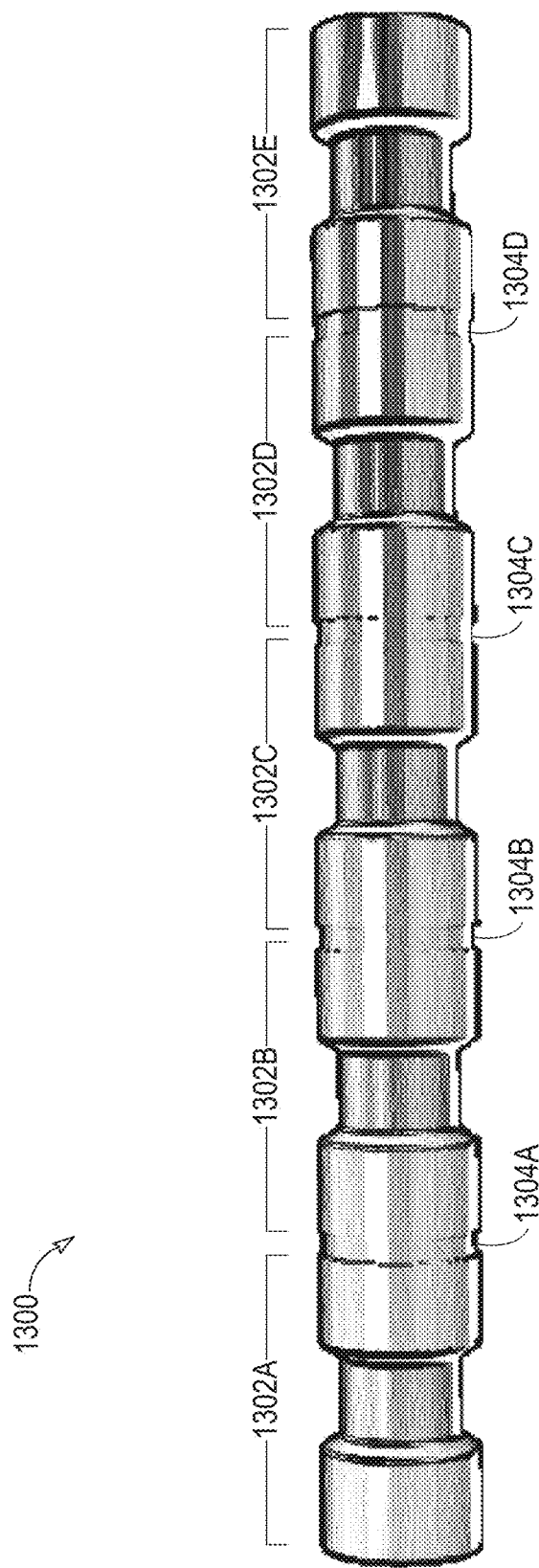
FIG. 13 shows a shortenable flexible element, in accordance with some examples.
Figure 14:
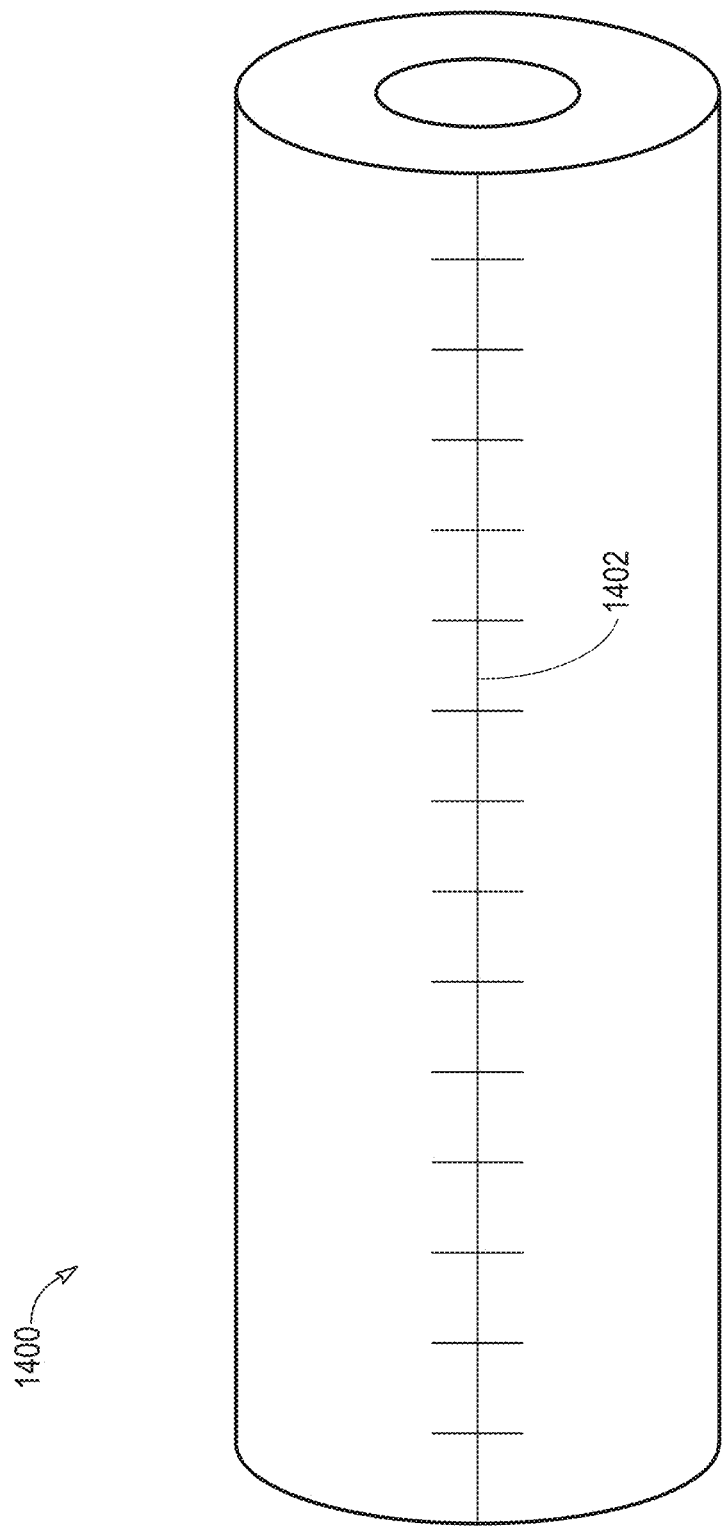
FIG. 14 shows another shortenable flexible element, in accordance with some examples.

In some examples, it can be desirable to shorten the flexible element to a desired length. FIGS. 13-14 show two examples of flexible elements that include features intended to aid in shortening the respective flexible elements. Shortening a flexible element to suit a particular patient can reduce a number of inventory elements needed to perform a surgery.

FIG. 13 shows a shortenable flexible element, in accordance with some examples. In the configuration of FIG. 13, the flexible element 1300 can be formed as a series of flexible elements 1302A-E that are joined end-to-end, so that they extend along a longitudinal path. Between each pair of adjacent flexible elements 1302A-E is a weakened portion 1304A-D. Each weakened portion 1304A-D can be formed with a diameter less than a diameter of the flexible elements 1302A-E at the longitudinal ends of the flexible elements 1302A-E. With such a reduced diameter, the flexible element 1300 can be broken into smaller portions. For example, when a practitioner breaks the flexible element 1300 at weakened portion 1304B, the flexible element 1300 can break into smaller flexible elements 1302A-B and 1302C-E. In some examples, the weakened portions 1304A-D can be formed so that a surgeon can cut along the weakened portions 1304A-D. For example, the weakened portions 1304A-D can be formed to accommodate a saw blade or a scalpel. In some examples, the weakened portions 1304A-D can guide a cutting instrument by having a reduced diameter, and optionally, a waist.

FIG. 14 shows another shortenable flexible element, in accordance with some examples. In the configuration of FIG. 14, the flexible element 1400 can include a graduated scale 1402 or cutting mark 1402 printed and/or textured on an exterior surface of the flexible element 1400. A surgeon can use the graduated scale 1402 or cutting mark 1402 to shorten the flexible element 1400 to a desired length, by cutting, sawing, grinding, or other suitable shortening technique. In some examples, the graduated scale 1402 of FIG. 14 can be used in combination with the shortenable flexible element 1300 of FIG. 13.

The flexible elements discussed thus far can be generally fixed in their flexibilities. Beyond adjusting for length, the flexible elements discussed above generally do not adjust their flexibilities once they are manufactured. As an option, there can be flexible elements that include a mechanism for adjusting their flexibilities.

Figure 15:
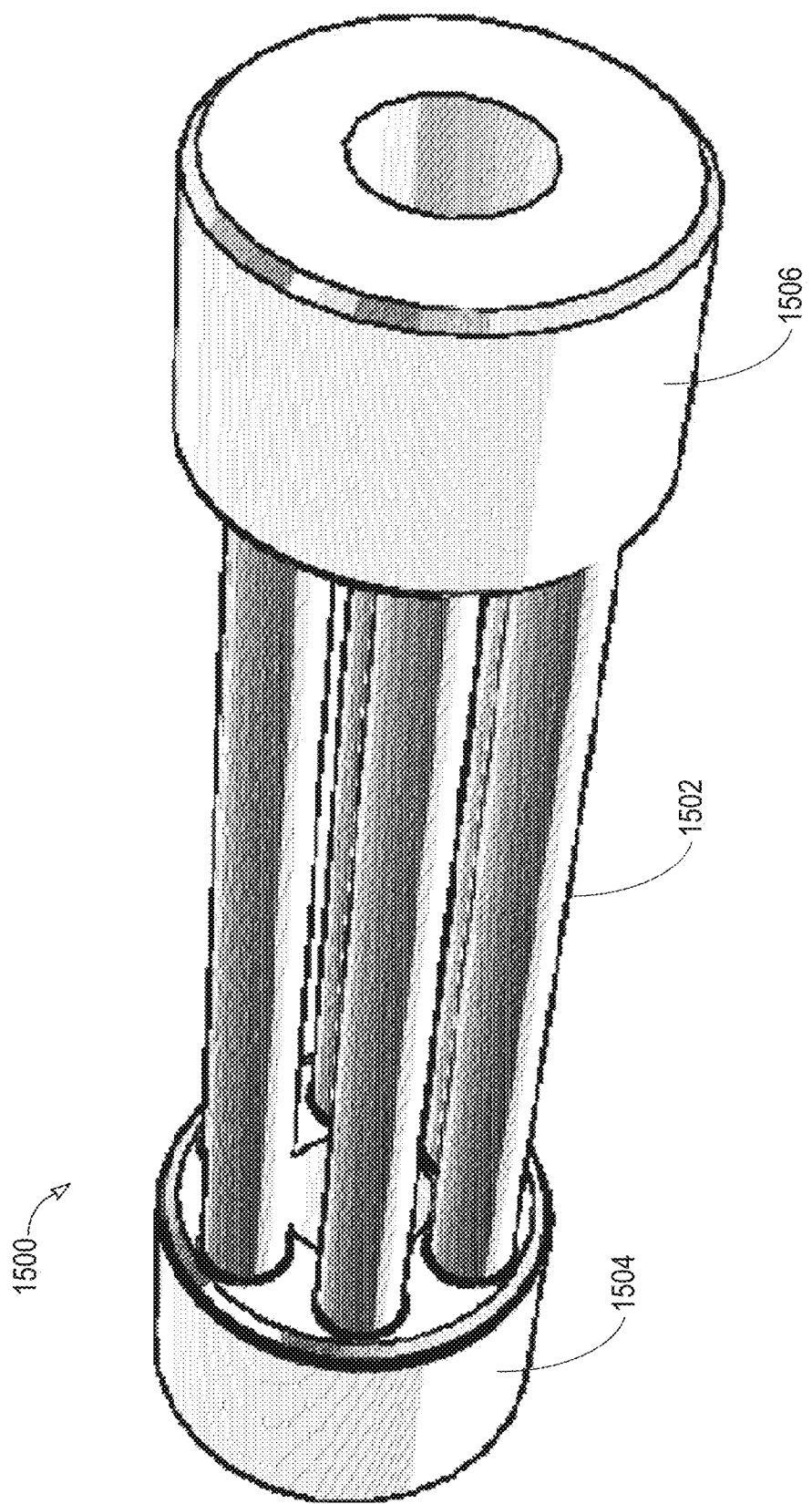
FIG. 15 shows a flexible element with an adjustable flexibility, in accordance with some examples.

For example, FIG. 15 shows a flexible element 1500 with an adjustable flexibility, in accordance with some examples. The configuration of FIG. 15 is but one example of shows a flexible element 1500 with an adjustable flexibility; other configurations can also be used.

The flexible element 1500 can include one or more strands 1502 that extend between a sternum-facing portion 1504 and a rib-facing portion 1506. In some examples, the strands 1502 extend in a longitudinal direction and are parallel to one another. In other examples, the strands 1502 can be interwoven with one another, such as in a braid or a rope-like pattern. In some examples, one or more strands 1502 can extend helically around a longitudinal axis of the flexible element 1500.

To adjust the flexibility of the flexible element 1500, a surgeon can cut one of more of the strands 1502. For example, the surgeon can cut a strand 1502 anywhere along a length of the strand 1502. In some examples, the surgeon can optionally cut a strand 1502 in two locations, and can optionally remove the portion of the strand 1502 between the cuts.

By cutting one or more strands 1502, the surgeon can increase the flexibility of the flexible element 1500. In some examples, for a relatively large number of strands 1502, the flexibility can be approximated as being linear with respect to the number of strands. For example, for a flexible element 1500 having ten strands 1502, cutting one of the ten strands 1502 can increase a flexibility of the flexible element 1500 by approximately 10%. This is not intended to be a precise calculation, but instead be a mere order-of-magnitude estimate.

In allowing the flexible element 1500 to have an adjustable flexibility, such by including strands 1502 that are individually cuttable, a surgeon can optionally require fewer configurations of flexible elements 1500 in a system or kit of flexible elements 1500. For example, a surgeon can install a pre-formed configuration with a flexibility slightly less the desired flexibility, and cut one or more strands 1502 of the flexible element 1500 until the desired flexibility is reached.

Figure 16:
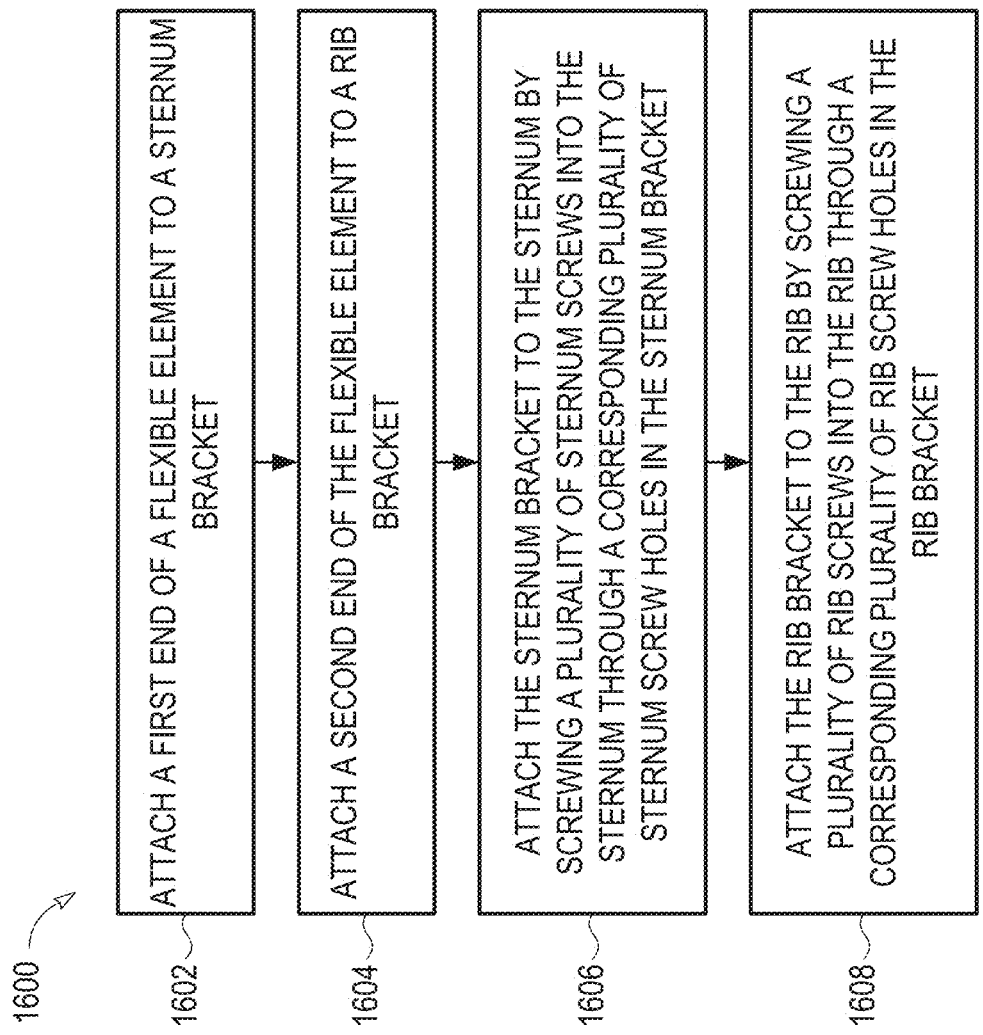
FIG. 16 shows a flowchart of a method for surgically attaching one or more ribs of a patient to a sternum of the patient, in accordance with some examples.

FIG. 16 shows a flowchart of a method 1600 for surgically attaching one or more ribs of a patient to a sternum of the patient, in accordance with some examples. The method 1600 can be executed by a surgeon implanting any of the system elements discussed above, or implanting any suitable system elements. The method 1600 is but one example of a method 1600 for surgically attaching one or more ribs of a patient to a sternum of the patient; other suitable methods can also be used.

At operation 1602, a surgeon can attach a first end of a flexible element to a sternum bracket, such as via a threaded connection.

At operation 1604, the surgeon can attach a second end of the flexible element to a rib bracket, such as via a threaded connection.

At operation 1606, after the sternum bracket, the flexible element, and the rib bracket are attached to one another, the surgeon can attach the sternum bracket to the sternum by fastening a plurality of sternum fasteners into the sternum through a corresponding plurality of sternum fastener holes in the sternum bracket. Examples of sternum fasteners can include screws, nails, staples, and others.

At operation 1608, after the sternum bracket, the flexible element, and the rib bracket are attached to one another, the surgeon can attach the rib bracket to the rib by fastening a plurality of rib fasteners into the rib through a corresponding plurality of rib fastener holes in the rib bracket. Examples of rib fasteners can include screws, nails, staples, and others.

In the foregoing detailed description, the method and apparatus of the present disclosure have been described with reference to specific embodiments thereof. It will, however, be evident that various modifications and changes may be made thereto without departing from the broader spirit and scope of the present disclosure. The present specification and figures are accordingly to be regarded as illustrative rather than restrictive.

To further illustrate the device and related method disclosed herein, a non-limiting list of examples is provided below. Each of the following non-limiting examples can stand on its own, or can be combined in any permutation or combination with any one or more of the other examples.

In Example 1, a system for surgically attaching a rib of a patient to a sternum of the patient can include: a rib bracket configured to fixedly attach to a sternal end of the rib; a sternum bracket configured to fixedly attach to the sternum; and a flexible element positionable to extend between the sternum bracket and the rib bracket.

In Example 2, the system of Example 1 can optionally be configured such that the flexible element has a durometer and a geometry that are selected such that the flexible element has a flexibility that matches a flexibility of natural human costal cartilage.

In Example 3, the system of any one of Examples 1-2 can optionally be configured such that the flexible element has a cross-sectional shape that includes one of round, oval, rectangular, or oblong.

In Example 4, the system of any one of Examples 1-3 can optionally be configured such that the flexible element has a hollow interior extending from a first end of the flexible element to a second end of the flexible element.

In Example 5, the system of any one of Examples 1-4 can optionally be configured such that the flexible element has a solid interior between a first end of the flexible element and a second end of the flexible element.

In Example 6, the system of any one of Examples 1-5 can optionally be configured such that the flexible element has a durometer that matches a durometer of natural human costal cartilage and a geometry that matches a geometry of natural human costal cartilage.

In Example 7, the system of any one of Examples 1-6 can optionally be configured such that the geometry of the natural human costal cartilage is, for a specified rib of the plurality of ribs in the human anatomy, based on an average patient size determined from measurements corresponding to a plurality of patients.

In Example 8, the system of any one of Examples 1-7 can optionally be configured such that the geometry of the natural human costal cartilage corresponds to a measured geometry of a specific patient.

In Example 9, the system of any one of Examples 1-8 can optionally be configured such that the flexible element has a first end that is connectable to the sternum bracket and a second end that is connectable to the rib bracket.

In Example 10, the system of any one of Examples 1-9 can optionally be configured such that the flexible element has a first end that is pre-attached to the sternum bracket and a second end that is connectable to the rib bracket.

In Example 11, the system of any one of Examples 1-10 can optionally be configured such that the flexible element has a first end that is connectable to the sternum bracket and a second end that is pre-attached to the rib bracket.

In Example 12, the system of any one of Examples 1-11 can optionally be configured such that the flexible element has a first end that is connectable to the sternum bracket via one of mating fastener threads, or a press fit that includes at least one retaining barb.

In Example 13, the system of any one of Examples 1-12 can optionally be configured such that the flexible element has a second end that is connectable to the rib bracket via one of mating fastener threads, or a press fit that includes at least one retaining barb.

In Example 14, the system of any one of Examples 1-13 can optionally be configured such that the flexible element has a first end that is overmolded onto to at least a portion of the sternum bracket.

In Example 15, the system of any one of Examples 1-14 can optionally be configured such that the flexible element has a second end that is overmolded onto to at least a portion of the rib bracket.

In Example 16, the system of any one of Examples 1-15 can optionally be configured such that the sternum bracket includes at least one sternum fastener hole shaped and sized to accommodate a sternum fixation fastener.

In Example 17, the system of any one of Examples 1-16 can optionally be configured such that the sternum bracket includes a plurality of sternum fastener holes, each sternum fastener hole being shaped and sized to accommodate a sternum fixation fastener.

In Example 18, the system of any one of Examples 1-17 can optionally be configured such that the sternum fastener holes are arranged in a line that extends in a plane of the rib.

In Example 19, the system of any one of Examples 1-18 can optionally be configured such that the sternum fastener holes are arranged along a curve that has a tangent at its center that extends orthogonal to a plane of the rib.

In Example 20, the system of any one of Examples 1-19 can optionally be configured such that the sternum bracket includes a male threaded portion configured to threadedly attach to a corresponding female threaded portion at a first end of the flexible element, the male threaded portion facing away from the sternum toward the rib when the flexible element is attached to the sternum bracket.

In Example 21, the system of any one of Examples 1-20 can optionally be configured such that the male threaded portion is colinear with a central axis of the rib.

In Example 22, the system of any one of Examples 1-21 can optionally be configured such that the sternum bracket includes a ledge shaped to fit against an intercostal region of the sternum.

In Example 23, the system of any one of Examples 1-22 can optionally be configured such that the rib bracket includes at least one rib fastener hole shaped and sized to accommodate a rib fixation fastener.

In Example 24, the system of any one of Examples 1-23 can optionally be configured such that the rib bracket includes a plurality of rib fastener holes, each rib fastener hole being shaped and sized to accommodate a rib fixation fastener.

In Example 25, the system of any one of Examples 1-24 can optionally be configured such that the rib fastener holes are arranged in a line that extends parallel to the rib.

In Example 26, the system of any one of Examples 1-25 can optionally be configured such that the sternal end of the rib is resected to expose an interior portion; and the rib bracket includes an intramedullary portion that is configured to extend at least partially into the interior portion.

In Example 27, the system of any one of Examples 1-26 can optionally be configured such that the rib bracket includes a male threaded portion configured to attach to a corresponding female threaded portion at a second end of the flexible element.

In Example 28, the system of any one of Examples 1-27 can optionally be configured such that the rib bracket includes a male threaded portion configured to threadedly attach to a corresponding female threaded portion at a second end of the flexible element, the male threaded portion facing away from the rib toward the sternum when the flexible element is attached to the rib bracket.

In Example 29, the system of any one of Examples 1-28 can optionally be configured such that the male threaded portion is colinear with a central axis of the rib.

In Example 30, the system of any one of Examples 1-29 can optionally be configured such that the sternal end of the rib is resected; and the rib bracket includes a ledge shaped to fit against the resected sternal end of the rib.

In Example 31, the system of any one of Examples 1-30 can optionally be configured such that the flexible element is positionable to extend between the sternum bracket and a single rib bracket.

In Example 32, the system of any one of Examples 1-31 can optionally be configured such that the rib bracket is one of a plurality of rib brackets that are configured to fixedly attach to a respective plurality of ribs of the patient; and the flexible element is positionable to extend between the sternum bracket and the plurality of rib brackets.

In Example 33, the system of any one of Examples 1-32 can optionally be configured such that the flexible element includes a first member positionable to extend to a first rib, a second member positionable to extend to a second rib, and a transverse member extending between the first and second members.

In Example 34, the system of any one of Examples 1-33 can optionally be configured such that the rib bracket is configured to fixedly attach to a resected sternal end of a first rib of a plurality of ribs of the patient; and further comprising: a second rib bracket configured to fixedly attach to a resected sternal end of a second rib of the plurality of ribs of the patient, the first and second ribs being at a same first longitudinal location along the sternum on opposite side of the sternum; and a second flexible element positionable to extend between the sternum bracket and the second rib bracket, wherein the sternum bracket is sized to extend across a lateral dimension of the sternum at the first longitudinal location along the sternum.

In Example 35, a method for surgically attaching one or more ribs of a patient to a sternum of the patient can include: threadedly attaching a first end of a flexible element to a sternum bracket; threadedly attaching a second end of the flexible element to a rib bracket; and after the sternum bracket, the flexible element, and the rib bracket are attached to one another: attaching the sternum bracket to the sternum by fastening a plurality of sternum fasteners into the sternum through a corresponding plurality of sternum fastener holes in the sternum bracket; and attaching the rib bracket to the rib by fastening a plurality of rib fasteners into the rib through a corresponding plurality of rib fastener holes in the rib bracket.

In Example 36, a system for surgically attaching a rib of a patient to a sternum of the patient can include: a sternum replacement implant configured to replace at least a portion of the sternum; a rib bracket configured to fixedly attach to a sternal end of the rib; and a flexible element positionable to extend between the sternum replacement implant and the rib bracket.

In Example 37, the system of Example 36 can optionally be configured such that the sternum replacement implant includes a first half and a second half, the first and second halves being laterally separable and reattachable.

In Example 38, the system of any one of Examples 2-34 can be optionally configured to include the configuration of Example 36.

In Example 39, the system of any of Examples 1-38 can optionally be configured such that the flexible element includes a plurality of strands extending between a sternum-facing portion and a rib-facing portion, the strands being cuttable to increase a flexibility of the flexible element.

What is claimed is:

1. A system for surgically attaching a rib of a patient to a sternum of the patient, the system comprising:
   a rib bracket configured to fixedly attach to a sternal end of the rib;
   a sternum bracket that includes a plurality of sternum fastener holes that are shaped and sized to accommodate corresponding sternum fixation fasteners that are configured to fixedly attach to the sternum through the corresponding sternum fastener holes; and
   a flexible element positionable to extend between the sternum bracket and the rib bracket.

2. The system of claim 1, wherein the flexible element has a durometer and a geometry that are selected such that the flexible element has a flexibility that substantially matches a flexibility of natural human costal cartilage.

3. The system of claim 1, wherein the flexible element is formed from silicone.

4. The system of claim 1, wherein the flexible element has a cross-sectional shape that includes one of round, oval, rectangular, or oblong.

5. The system of claim 1, wherein the flexible element has a hollow interior extending from a first end of the flexible element to a second end of the flexible element.

6. The system of claim 1, wherein the flexible element has a solid interior between a first end of the flexible element and a second end of the flexible element.

7. The system of claim 1, wherein, for a specified rib of the plurality of ribs in the human anatomy, the flexible element has a geometry of the natural human costal cartilage is based on an average patient size determined from measurements corresponding to a plurality of patients.

8. The system of claim 1, wherein the flexible element has a geometry that corresponds to a measured geometry of a specific patient.

9. The system of claim 1, wherein the flexible element has a first end that is connectable to the sternum bracket and a second end that is connectable to the rib bracket.

10. The system of claim 1, wherein the flexible element has a first end that is pre-attached to the sternum bracket and a second end that is connectable to the rib bracket.

11. The system of claim 1, wherein the flexible element has a first end that is connectable to the sternum bracket and a second end that is pre-attached to the rib bracket.

12. The system of claim 1, wherein the sternum bracket includes a ledge shaped to fit against an intercostal region of the sternum.

13. The system of claim 1, wherein
the sternum fastener holes are arranged in a line that extends in a plane of the rib.

14. The system of claim 1, wherein
the sternum fastener holes are arranged along a curve that has a tangent at its center that extends orthogonal to a plane of the rib.

15. The system of claim 1, wherein:
the rib bracket includes a plurality of rib fastener holes;
each rib fastener hole is shaped and sized to accommodate a rib fixation fastener; and
the rib fastener holes are arranged in a line that extends parallel to the rib.

16. The system of claim 1, wherein the rib bracket includes a ledge shaped to fit against a resected sternal end of the rib.

17. The system of claim 1, wherein the rib bracket includes an intramedullary portion that is configured to extend at least partially into an interior portion of a resected rib.

18. The system of claim 1, wherein the rib bracket is configured to fixedly attach to a resected sternal end of a first rib of a plurality of ribs of the patient; and further comprising:
   a second rib bracket configured to fixedly attach to a resected sternal end of a second rib of the plurality of ribs of the patient, the first and second ribs being at a same first longitudinal location along the sternum on opposite side of the sternum; and
   a second flexible element positionable to extend between the sternum bracket and the second rib bracket,
   wherein the sternum bracket is sized to extend across a lateral dimension of the sternum at the first longitudinal location along the sternum.

19. The system of claim 1, where the flexible element includes a plurality of strands extending between a sternum-facing portion and a rib-facing portion, the strands being cuttable to increase a flexibility of the flexible element.

20. A method for surgically attaching one or more ribs of a patient to a sternum of the patient, the method comprising:
   attaching a first end of a flexible element to a sternum bracket;
   attaching a second end of the flexible element to a rib bracket;
   attaching the sternum bracket to the sternum by fastening a plurality of sternum fasteners into the sternum through a corresponding plurality of sternum fastener holes in the sternum bracket; and attaching the rib bracket to the rib by fastening a plurality of rib fasteners into the rib through a corresponding plurality of rib fastener holes in the rib bracket.

\* \* \* \* \*